United States Patent [19]

McEwen

[11] Patent Number: 4,869,265
[45] Date of Patent: Sep. 26, 1989

[54] BIOMEDICAL PRESSURE TRANSDUCER

[75] Inventor: James A. McEwen, Richmond, Canada

[73] Assignee: Western Clinical Engineering Ltd., Vancouver, Canada

[21] Appl. No.: 33,770

[22] Filed: Apr. 3, 1987

[51] Int. Cl.$^4$ .............................................. A61B 5/10
[52] U.S. Cl. ................................... 128/774; 128/748; 128/327
[58] Field of Search .................... 128/748, 774–782, 128/341–345, DIG. 20, 327, 686; 200/83 N, 83 Y, 81.4, 211, 212, 214

[56] References Cited

U.S. PATENT DOCUMENTS

| | | | |
|---|---|---|---|
| 3,095,873 | 7/1963 | Edmunds | 128/2.05 |
| 3,209,089 | 9/1965 | Weissbury | 200/83 N |
| 3,958,562 | 5/1976 | Hakim et al. | 128/748 |
| 4,114,603 | 9/1978 | Wilkinson | 128/748 |
| 4,147,161 | 4/1979 | Ikebe et al. | 128/748 |
| 4,217,473 | 8/1980 | Parkinson | 200/159 B |
| 4,218,600 | 8/1980 | Kissner | 200/159 B |
| 4,299,230 | 11/1981 | Kubota | 128/748 |
| 4,300,029 | 11/1981 | Maser | 200/159 B |
| 4,378,809 | 4/1983 | Cosman | 128/748 |
| 4,385,636 | 5/1983 | Cosman | 128/748 |
| 4,469,099 | 9/1984 | McEwen | 128/327 |
| 4,476,871 | 10/1984 | Hon | 128/778 |
| 4,479,494 | 10/1984 | McEwen | 128/327 |
| 4,605,010 | 8/1986 | McEwen | 128/686 |
| 4,770,175 | 9/1988 | McEwen | 128/327 |

OTHER PUBLICATIONS

"The Pressure Distribution Under Tourniquets", McLaren et al., The J. of Bore & Jt. Surgery, Incorp., Mar. 1985.
J. A. McEwen and R. W. McGraw, "An adaptive Tourniquet for Improved Safety in Surgery", IEEE Trans. Bio-Med Eng., vol. BME29, 1982, pp. 122–128.
J. A. McEwen and G. F. Auchinleck, "Advances in Surgical Toruniquets," J.A.O.R.N., vol. 36, 1982, pp. 889–896.
J. A. Shaw and D. G. Murray, "The Relationship Between Tourniquet Pressure and ... ", J. Bone & Joint Surg., vol. 64–A, 1982, pp. 1148–1152.
A. C. McLaren and C. H. Rorabeck, "The Pressure Distribution Under Tourniquets," J. Bone & Joint Surg.,m 67A, 1985, pp. 433–438.
R. J. Newman and A. Muirhead, "A Safe & Effective Low Press. Tourniquet", J. Bone & Joint Surg., 68B, 1986, pp. 625–628.
J. A. Shaw et al., "Guidelines for the Use of Digital Tourniquets ... ", J. Bone & Joint Surg., 67A, 1985, pp. 1086–1090.
S. E. Grice et al., "Intravenous Regional Anesthesia: Evaluation and Prevention of Leakage ... ", Anesthesiology, 65, pp. 316–320, 1986.

Primary Examiner—Max Hindenburg

[57] ABSTRACT

A biomedical transducer which is useful for interposing between a tissue and apparatus or another tissue or organ which is applying pressure to the tissue, in order to estimate the pressure applied to a selected area of the tissue. The biomedical pressure transducer comprises: a first flexible layer carrying at least one electrical contact; a second flexible layer carrying at least one electrical contact and cooperating with the first flexible layer to define a pressurizable chamber wherein the contacts are normally touching when the chamber is not pressurized; and pressure estimation means for selectably pressurizing the pressurizing chamber so as to move at least one of said flexible layers sufficiently to separate the electrical contacts, and for indicating the lowest selected pressure at which the contacts are separated.

17 Claims, 5 Drawing Sheets

BIOMEDICAL PRESSURE TRANSDUCER

FIELD OF THE INVENTION

This invention pertains to transducers for estimating the pressure applied to a tissue of a body by an object such as a medical device or body part. The invention particularly pertains to a thin and flexible transducer useful in health care for interposing at the surface between a tissue and an object, without substantially displacing either the tissue or the object from the surface, to estimate the pressure applied near at least one predetermined tissue location.

BACKGROUND OF THE INVENTION

There are many clinical situations in which it is desirable to have an accurate estimate of the pressure applied to a tissue of a body by a medical device or by a body part such as another tissue or organ. These clinical situations include: the evaluation of new and existing types of occlusive cuffs for pneumatic tourniquet systems and sphygmomanometers; the evaluation, improvement and standardization of the techniques employed by clinical staff in selecting and snugly applying an occlusive cuff to an extremity having a particular size, shape and tissue composition; the development and evaluation of innovative and potentially less expensive automatic tourniquet systems, including non-pneumatic tourniquet systems; the development and evaluation of advanced robotic devices and pre-robotic devices for tissue manipulation and limb manipulation in surgery and rehabilitation; the development and evaluation of improved, safer systems for a common anesthetic technique (intravenous regional anesthesia) which is based on the proper use of a special occlusive cuff; the development, improvement and evaluation of biomechanical models of tissue; the evaluation and fitting of special dressings and garments for applying pressure within a pressure-tolerance window to the tissue of burn patients in order to enhance healing; the diagnosis and treatment of compartmental pressure syndrome in orthopedics; the monitoring and control of sequential limb compression devices for prevention of deep venous thrombosis, and medical anti-shock trousers for emergency treatment; and perhaps the investigation and treatment of pressure sores in immobile patients.

Different types of biomedical pressure transducers known in the prior art may have a number of disadvantages when used in clinical situations such as those described above. First, many transducers known in the prior art are not sufficiently thin and flexible for interposing between selected body tissues and objects such as medical devices or body parts, e.g. organs, skeletal structures and other tissues, without displacing substantially either the tissue or the object. Transducers which require a rigid substrate for proper operation are not particularly useful for estimating the pressure applied to one soft tissue by an adjacent soft tissue, or for estimating the pressure applied to the tissue by an object having a curved or irregular surface. Many types of transducers known in the prior art are mass-produced in one standard form using expensive fabrication technologies to achieve economies of scale, and thus these transducers cannot be readily adapted. Adaption is important in many biomedical situations: it is frequently desirable to have a transducer array, or a plurality of transducers, for simultaneously estimating the pressures at a plurality of predetermined locations of a tissue beneath a pressure-applying object; and it is often desirable to change the number and area of the pressure transducers at those locations for selected combinations of tissues and objects. Similarly, in many prior art transducers which are mass-produced in one standard form, the composition and physical dimensions of various elements of these transducers cannot be conveniently and economically modified so that the transducer conforms more closely between a particular tissue and object of interest. Many of the biomedical pressure transducers known in the prior art are inherently complex and expensive, thus reducing the probability that such transducers might be conveniently and economically integrated if desired into medical devices such as occlusive cuffs, pressure dressings for burn patients, tissue retractors and the patient-applied parts of robotic systems for surgery and rehabilitation. Other transducers known in the prior art have the disadvantage that they cannot be conveniently sterilized by commonly used techniques, and this precludes the use of such prior-art transducers inside the body, either between adjacent soft tissues (e.g. in the diagnosis and treatment of compartmental pressure syndrome), or in surgery (e.g. between a soft tissue and an object such as a tissue retractor). Some transducers known in the prior art require complex and expensive support circuitry, and others require difficult and time-consuming calibration procedures. Another disadvantage of some prior-art transducers is that their accuracy and hysteresis cannot be conveniently checked by clinical staff in a health-care environment using readily available apparatus and electronic pressure transducers. A final disadvantage of certain biomedical pressure transducers is that, because of unacceptable inaccuracy, calibration difficulties or unreliability associated with repetitive usage, these transducers cannot be safely incorporated into systems for automatically controlling the pressure applied to a body tissue near a predetermined location.

The biomedical pressure transducer of the present invention was developed to overcome many of the disadvantages of prior-art transducers for clinical situations such as those indicated above. The transducer of the present invention makes advantageous use of some of the technology developed for, and now commonly employed in, the fabrication of inexpensive and flexible membrane switches in small batches for a wide variety of applications.

The applicant is aware of the following United States patents which are more or less relevant to the subject matter of the applicant's invention.

| | | | | |
|---|---|---|---|---|
| 4,605,010 | 8/1986 | McEwen | | 128/686 |
| 4,479,494 | 10/1984 | McEwen | 128/327 | 128/682 |
| 4,469,099 | 9/1984 | McEwen | 128/327 | 128/682 |
| 4,300,029 | 11/1981 | Maser | | 200/159B |
| 4,218,600 | 8/1980 | Kissner | 200/159B | |
| 4,217,473 | 8/1980 | Parkinson | 200/159B | |
| 3,095,873 | 7/1963 | Edmunds | 128-2.05 | |

The following U.S. patent applications of the applicant are more or less relevant to the subject matter of the applicant's invention.

U.S. application Ser. No. 921,461; Title-Occlusive Cuff; Art Unit-335; Inventor-McEwen.

U.S. continuation-in-part-application Ser. No. 831,001; Title-Advanced Medical Robot; Art Unit 335; Inventors: McEwen et al.

U.S. application Ser. No. 006,131; Title-Patient Limb Positioning Apparatus; Art Unit-N/A; Inventors: Auchinleck, McEwen et al.

The applicant is also aware of the following published references which are more or less relevant to the subject matter of the applicant's invention.

J. A. McEwen and R. W. McGraw, "An adaptive tourniquet for improved safety in surgery." IEEE Transactions in Biomedical Engineering, Vol.BME-29, February 1982, pp. 122-128.

J. A. McEwen and G. F. Auchinleck, "Advances in surgical tourniquets." J. Assn. Operating Room Nurses, Vol. 36, 1982, pp. 889-896.

J. A. Shaw and D. G. Murray, "The relationship between tourniquet pressure and underlying soft-tissue pressure in the thigh." The Journal of Bone and Joint Surgery, Vol. 64-A, 1982, pp. 1148-1152.

A. C. McLaren and C. H. Rorabeck, "The pressure distribution under tourniquets." The Journal of Bone and Joint Surgery, Vol. 67-A, 1985, pp. 433-438.

R. J. Newman and A. Muirhead, "A safe and effective low pressure tourniquet." Journal of Bone and Joint Surgery, Vol. 68-B, 1986, pp. 625-628.

J. A. Shaw, W. W. Demuth, an A. W. Gillespy, "Guidelines for the use of digital tourniquets based on physiological pressure measurements." The Journal of Bone and Joint Surgery, Vol. 67-A, 1985, pp. 1086-1090.

S. E. Grice et al., "Intravenous regional anesthesia Evaluation and prevention of leakage under the tourniquet." Anesthesiology, Vol. 65, pp. 316-320, 1986.

SUMMARY OF THE INVENTION

The invention is directed toward a transducer for estimating the pressure applied to a body tissue near a predetermined tissue location by an object such as a medical device or body part, comprising: a first flexible layer carrying a first electrical contact; a second flexible layer carrying a second electrical contact and cooperating with the first flexible layer to define a flexible pressurizable chamber for interposing between a tissue and an object wherein the first and second electrical contacts are touching near a predetermined tissue location when the chamber is not pressurized; and pressure estimation means for selectably pressurizing the chamber, and for indicating the lowest selected pressure at which the contacts are separated.

The pressure estimation means may include means for selectably depressurizing the chamber from a level at which the contacts are separated and for indicating the highest selected pressure at which the contacts touch. The chamber may surround the contacts. The contacts may be located near the longitudinal axis of the chamber. The first and second flexible layers may be formed of material that is substantially inextensible.

The chamber may be remote from the pressure estimation means and the cooperating first and second flexible layers may also define fluid passageway means for coupling the chamber surrounding the contacts to the remote pressure estimation means. The pressure estimation means may include electrical circuit means for determining remotely whether the contacts are touching or separated. The electrical circuit means may include electrically conductive lead means carried by at least one of the cooperating first and second flexible layers.

In clinical usage of the invention, the tissue and the object may be predetermined and may meet along a predetermined surface when the chamber is not interposed, and the layers defining the chamber may have physical dimensions and flexibility selected so that interposing chamber conforms to the surface without displacing substantially the tissue or object from the surface.

The invention is also directed toward a transducer for estimating the pressure applied to a body tissue near a plurality of predetermined tissue locations by an object such as a medical device or body part, comprising: a first flexible layer carrying a plurality of first electrical contacts; a second flexible layer carrying a plurality of second electrical contacts and cooperating with the first flexible layer to define a flexible pressurizable chamber for interposing between a tissue and an object, wherein pairs of first and second electrical contacts are touching near predetermined tissue locations when the chamber is not pressurized; and pressure estimation means for selectably increasing the pressure in the chamber and for indicating the lowest selected pressure at which each pair of contacts is separated.

The invention is also directed toward a system which uses the transducer for controlling the pressure applied to a body tissue near a predetermined tissue location comprising: pressure-applying means responsive to a pressure control signal for applying pressure to a tissue near a predetermined location; transducing means comprised of a first flexible layer carrying a first electrical contact, a second flexible layer carrying a second electrical contact and cooperating with the first flexible layer to define a flexible pressurizable chamber interposed between the tissue and the pressure-applying means wherein the first and second electrical contacts are touching near the predetermined location when the chamber is not pressurized, and pressure estimation means for selectably pressurizing the chamber, and for producing an applied pressure signal representative of the lowest pressure at which the first and second electrical contacts are separated; and pressure-regulating means responsive to the applied pressure signal for producing a pressure control signal to maintain the pressure applied to the tissue by the pressure-applying means near a predetermined reference pressure.

BRIEF DESCRIPTION OF THE DRAWINGS

A specific embodiment of this invention has been chosen for purposes of illustration and description wherein.

DESCRIPTION OF THE SPECIFIC EMBODIMENT

The specific embodiment illustrated is not intended to be exhaustive or to limit the invention to the precise form disclosed. It is chosen and described in order to explain the principles of the invention and its application and practical use, and thereby enable others skilled in the art to utilize the invention.

Figure 2:
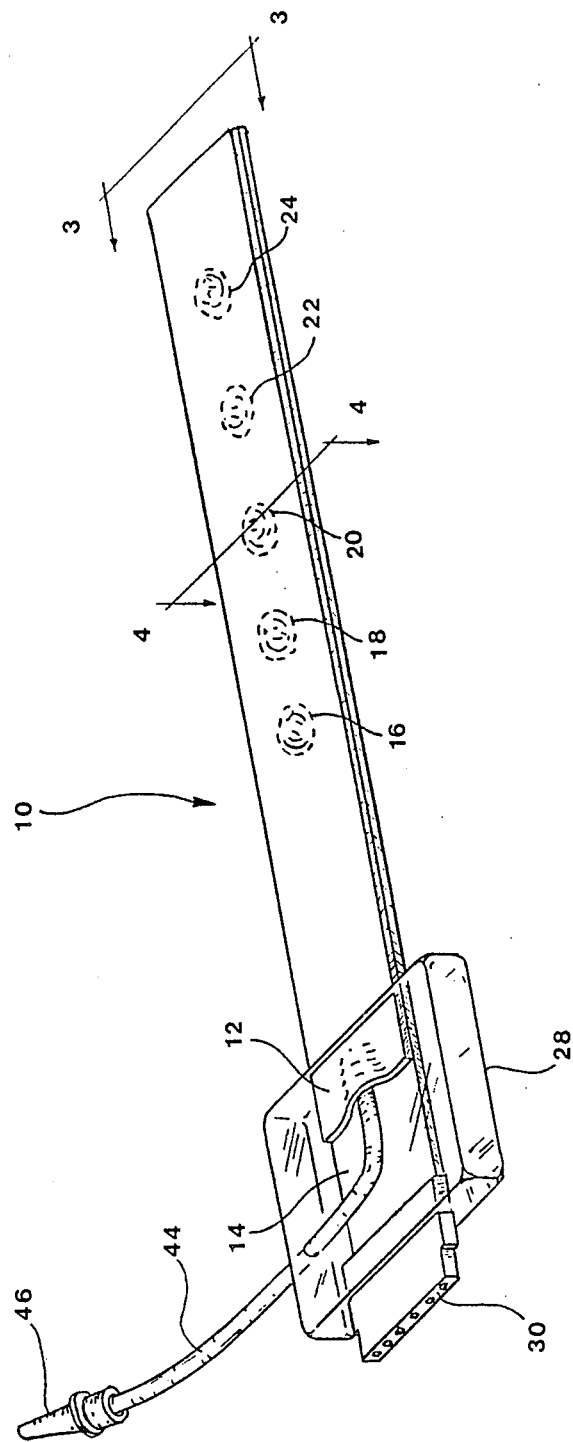
FIG. 2 is a perspective view of the transducer of FIG. 1.

The biomedical pressure transducer 10 of this invention, as can be seen in FIG. 2, includes upper contact support layer 12 and lower contact support layer 14 which have a similar, generally rectangular shape and which are made of flexible, inextensible transparent polyester known as Mylar (DuPont trademark) that is approximately 5 mils thick.

Figure 3:
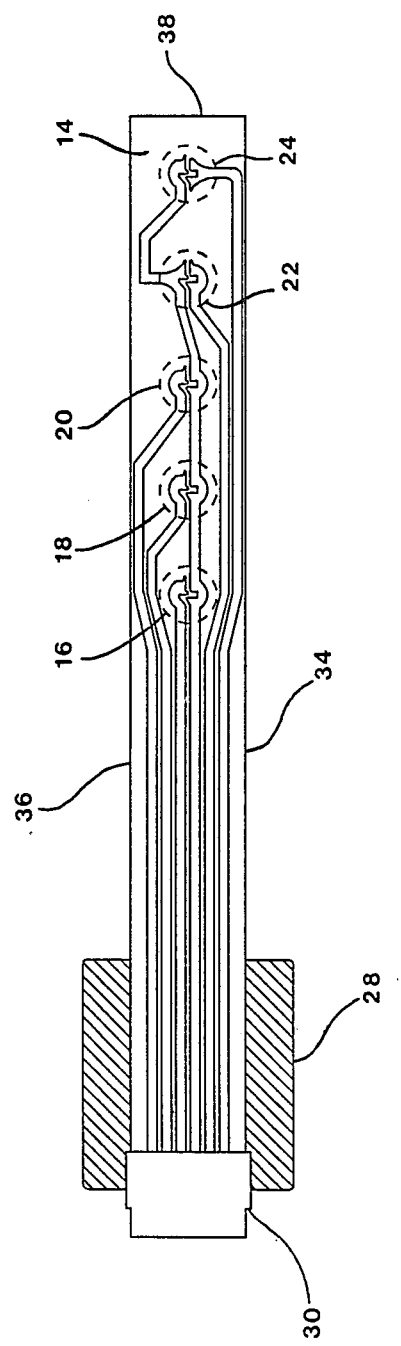
FIG. 3 is a sectional view taken along line 3—3 of FIG. 2.
Figure 4A:
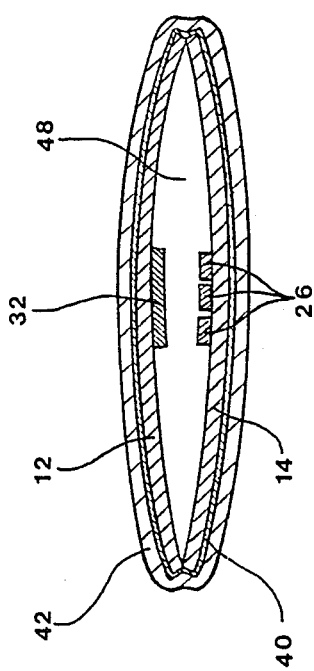
FIGS. 4A and 4B are sectional views taken along line 413 4 of FIG. 2 while the transducer is not pressurized, and while the transducer is pressurized, respectively.

FIG. 3 shows lower contact support layer 14 which has five circular switch contact areas 16, 18, 20, 22 and 24. In each switch contact area on lower contact support layer 14 are adjacent switch contacts 26 formed of a pattern of conductive silver ink (Electrodag 415SS, manufactured by Acheson Colloids, Port Huron, MI) having a thickness of approximately 0.4 mils and connected to leads of similar thickness formed of conductive silver ink which go through connecting block 28 to electrical connector 30. On upper contact support layer 12 directly over each of switch contact areas 16, 18, 20, 22 and 24 of lower contact support layer 14 is an upper switch contact 32 formed of a pattern of conductive silver ink having a thickness of about 0.4 mils and designed to short and form an electrical connection between adjacent switch contacts 26 on lower contact support layer 14 when the two layers are pressed together, as shown in FIG. 4A. Thus adjacent switch contacts 26 at each of the five switch contact areas 16 to 24 on lower contact support layer 14, together with the shorting upper switch contact 32 on upper contact support layer 12, form five switches located within switch contact areas 16, 18, 20, 22 and 24 near the longitudinal axis of layers 12 and 14. The five switches formed in this manner are normally closed, i.e. upper switch contact 32 is touching and shorting electrically adjacent switch contacts 26, when the upper and lower contact support layers 12 and 14 are pressed together. For the specific embodiment, upper contact support layer 12, lower contact support layer 14 and electrical connector 30 were conveniently obtained by disassembling and modifying components of a commercially available membrane switch (Brady Xymox 1×5 Membrane Switch Unit manufactured by W.H. Brady Co., Milwaukee, WI).

Upper and lower contact support layers 12 and 14 were sealed together along edges 34 and 36 from approximately 1 cm below electrical connector 30 to distal end 38 by first wrapping flexible, transparent adhesive tape 40 (Highland Type "371" Tape manufactured by the 3M Company, St. Paul, Minn.) around the outer surfaces of upper and lower contact support layers 12 and 14 as shown in FIG. 4A. Care was taken to seal tape 40 thoroughly to itself at distal end 38, and to assure that the entire outer surfaces of upper and lower contact support layers 12 and 14 adhered firmly to tape 40. The taped portion of layers 12 and 14 was then repeatedly dipped in a rubber coating liquid (Plasti Dip Flexible Air Dry Rubber Coating manufactured by PDI Inc., St. Paul, MN) which dried in air to form a thin, flexible, transparent sheath 42 which was fluid-tight and which enabled the taped and sheathed portion of transducer 10 to withstand repeated pressurization to more than 600 mmHg without leaking or rupturing.

Figure 4B:
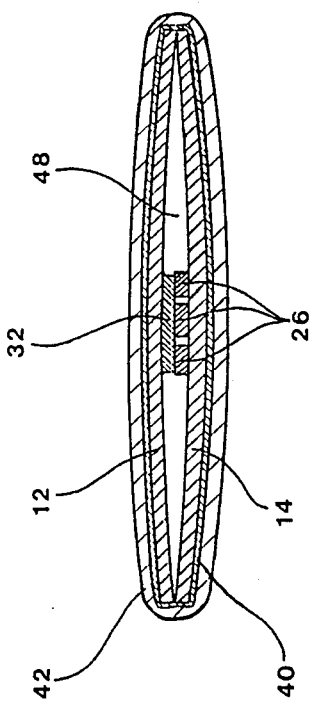

After sheath 42 was applied, the sheathed layers were positioned in relation to connecting block 28 as shown in FIG. 2. A short length of clear vinyl tubing 44 with male Luer-lock fitting 46 attached at one end was inserted through a side of connecting block 28 and then between upper and lower contact support layers 12 and 14, as shown in FIG. 2. After tubing 44 was inserted, connecting block 28 was filled with a clear epoxy resin which, when it cured, formed a strong, fluid-tight seal at the proximal end of transducer 10, thus establishing a pressurizable chamber 48 shown in FIGS. 4A and 4B. Pressurizable chamber 48 extends along substantially all of the length of sheathed contact support layers 12 and 14 and surrounds all switch contact areas 16 to 24 due to the non-zero thickness of the switch contacts and leads, as shown in FIG. 4A, and can be pressurized via the conduit means comprised of tubing 44 and Luer-lock fitting 46.

Figure 1:
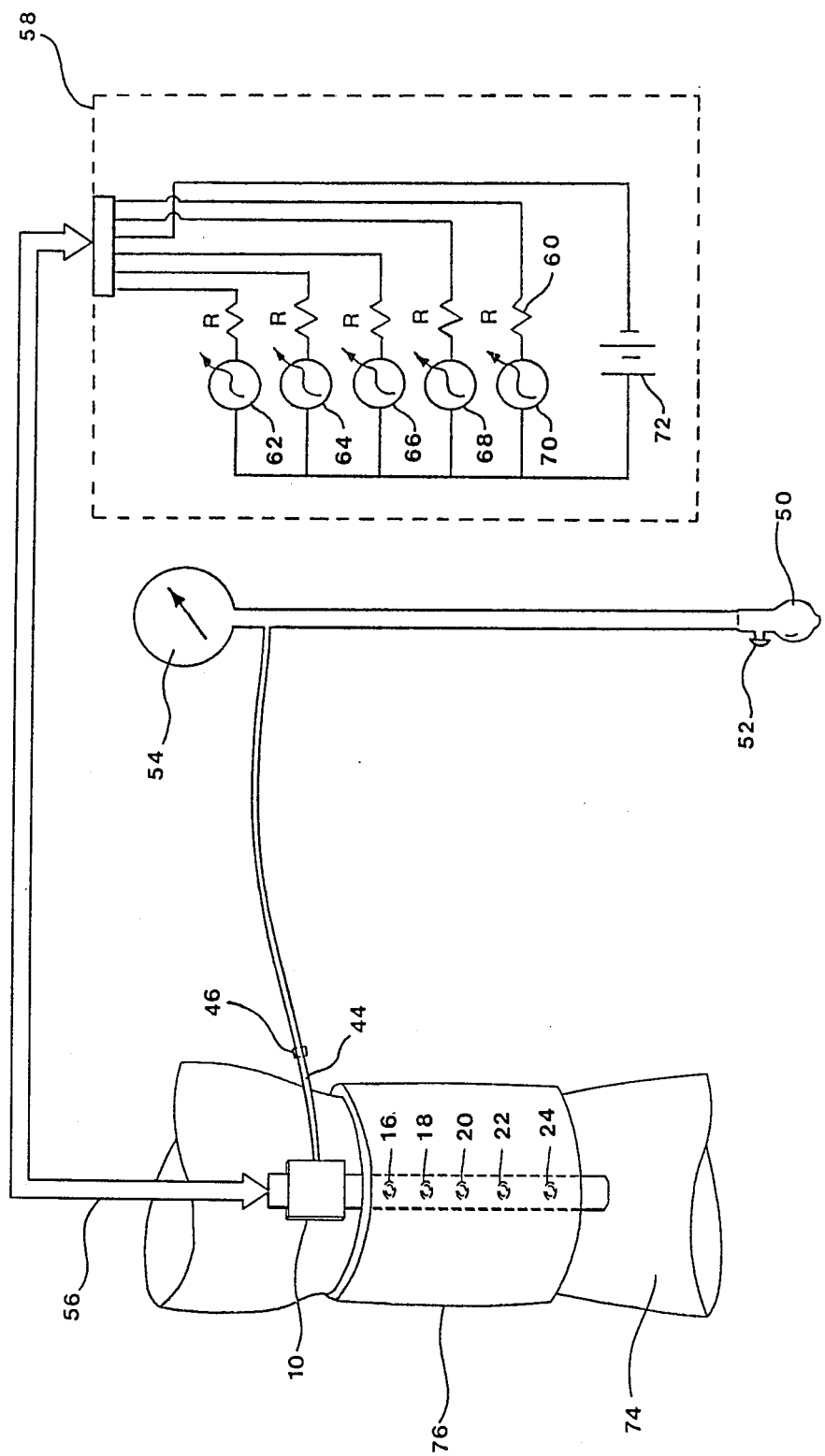
FIG. 1 is a schematic diagram depicting the biomedical pressure transducer of this invention.

As shown in FIG. 1, in order to use transducer 10, fitting 46 is first coupled to pressurizing means 50, depressurizing means 52, and pressure-indicating means 54. In the specific embodiment, pressurizing means 50 was a hand bulb from an aneroid sphygmomanometer set, depressurizing means 52 was a manual bleed valve attached to the hand bulb, and pressure-indicating means 54 was an aneroid pressure gage. Although pressurized air is described in the specific embodiment, any pressurized fluid that is non-conductive electrically and non-reactive chemically may be employed. Transducer 10 is connected via electrical cable 56 to electrical circuitry 58, as shown in FIG. 1. Electrical circuitry 58, which includes five similar current-limiting resistors 60, five light-emitting diodes 62, 64, 66, 68 and 70, and battery 72, connects the switch contacts in each of the five switch contact areas 16 through 24 to a corresponding light-emitting diode so that light is emitted when the corresponding switch contacts are touching, i.e. when the corresponding switch is in its normally closed state.

In the simplest typical clinical application illustrated in FIG. 1, transducer 10 is interposed between the surface of extremity 74 and occlusive band 76 which encircles and applies pressure to extremity 74. Transducer 10 is designed to be sufficiently thin, narrow and flexible so that it does not displace substantially the tissue of extremity 74 from its normal location in relation to occlusive band 76, and is designed to be sufficiently long to extend above and below the edges of occlusive band 76 and to have switch contact areas 16, 18, 20, 22, and 24 positioned at proximal, mid-proximal, middle, mid-distal, and distal locations, respectively, in relation to occlusive band 76. If desired, the relative locations of the switch contact areas 16 to 24 with respect to occlusive band 76 may be fixed temporarily by attaching transducer 10 to the inner surface of occlusive band 76 with double-sided adhesive tape. While the pressurizable chamber 48 of transducer 10 is not pressurized, all switch contacts are touching i.e. all switches are in their normally closed state, and all light-emitting diodes 62 to 70 emit light. Pressurizable chamber 48 of transducer 10 is then gradually pressurized by an operator activating pressurizing means 50, who observes the status of light-emitting diodes 62 through 70 and at the same time observes the pressure indicated by pressure-indicating means 54. The lowest pressure at which each light-emitting diode stops emitting light is recorded: each pressure thus recorded is an estimate of the pressure applied by occlusive band 76 in a normal direction onto the surface of extremity 74 beneath the corresponding switch contact area. Once pressurizable chamber 48 of transducer 10 has been pressurized sufficiently to extinguish all light-emitting diodes, the operator may use depressurizing means 52 to gradually depressurize chamber 48 of transducer 10 and record the highest pressure at which each of the light-emitting diodes begins emitting light, thus providing a second estimate of the pressure applied in a normal direction beneath the corresponding switch contact area and also providing (by comparison with the corresponding estimate obtained previously while pressure was increasing) an estimate of any inherent hysteresis that may exist in transducer 10 and in the other elements of the pressure estimation system. The set of pressure estimates obtained by manually pressurizing and depressurizing pressurizable chamber 48 of transducer 10 as described above is of intrinsic significance in many clinical applications.

Figure 5:
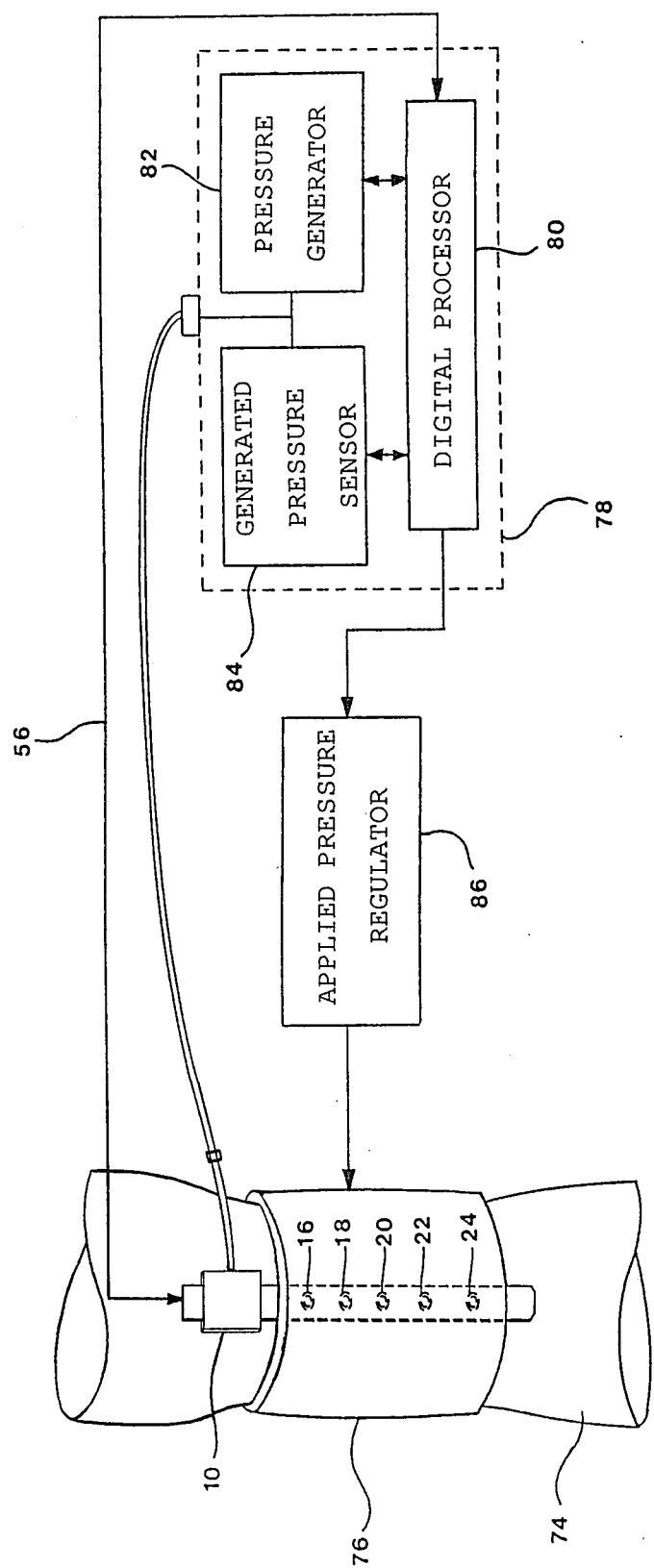
FIG. 5 is a block diagram of the transducer connected to electrical circuitry and apparatus for controlling the pressure applied by an occlusive band to a predetermined tissue location.

For more complex clinical applications where repetitive pressure estimates are required by a clinical operator, or where it is desired by the operator to automatically maintain the pressure applied to the surface of tissue beneath a selected switch contact area near a predetermined reference pressure, transducer 10 is attached to automated transducer controller 78 as shown in FIG. 5. Automated transducer controller 78 includes digital processor 80 for selectably pressurizing and depressurizing pressurizable chamber 48 of transducer 10 by controlling pressure generator 82, comprised of an electric pump and electrical pressure-relief valve. Digital processor 80 estimates the pressures applied to the surface of tissue beneath switch contact areas by reading the level of the signal produced by generated pressure sensor 84 as the switches at switch contact areas 16 to 24, which are monitored via electrical cable 56, change states during predetermined pressurization and depressurization cycles. Digital processor 80 produces an output signal representative of the pressures applied at the switch contact areas for display to an operator, and if desired for controlling applied pressure regulator 86 in order to maintain the pressure applied to an area of the surface of extremity 74 beneath a selected switch contact area near a predetermined reference pressure.

An evaluation of the accuracy and hysteresis of transducer 10 may be performed by an operator when desired by placing transducer 10 on a flat surface, applying a series of known pressures to the upper surface of transducer 10 at selected switch contact areas, pressurizing and depressurizing pressurizable chamber 48 of transducer 10, recording the pressures at which the switches change state, and comparing the recorded pressures to the known pressures.

As will be apparent to those skilled in the art, in the light of the foregoing disclosure many alterations and modifications are possible in the practice of this invention without departing from the scope or spirit thereof. For example, a smaller or larger number of switch contact areas could be included, and the size, spacing and patterns of the switch contact areas could be modified for a specific clinical application, as could the physical dimensions and type of material used to form the upper and lower switch contact support layers. As other examples: another method of sealing the upper and lower contact support layers around the edges, such at heat sealing, may be better suited for manufacture than taping, sheathing and potting in epoxy as described; and for some clinical applications it may be preferable to couple tubing to both ends of the transducer chamber to permit pressurization from both ends simultaneously, or to couple tubing to the middle of the transducer chamber to permit pressurization from the midpoint if, for example, the transducer were to be interposed circumferentially rather than transversely between an occlusive band and an extremity. Accordingly, the scope of the invention is to be construed in accordance with the substance defined by the following claims.

I claim:

1. Apparatus for estimating a pressure applied to a limb by a tourniquet cuff which encircles the limb, comprising:
   a first flexible layer carrying a first electrical contact;
   a second flexible layer carrying a second electrical contact and cooperating with the first flexible layer to define a flexible pressurizable chamber wherein the first and second electrical contacts are touching when the chamber is not pressurized;
   locating means for attaching the chamber to a tourniquet cuff in a position that interposes the chamber between the cuff and limb encircled by the cuff and locates the contacts near a predetermined cuff location; and
   pressure estimation means for selectably pressurizing the chamber, and for indicating the lowest selected pressure at which the contacts are separated.

2. Apparatus as defined in claim 1 wherein the pressure estimation means includes means for selectably depressurizing the chamber from a level at which the contacts are separated and for indicating the highest selected pressure at which the contacts touch.

3. Apparatus as defined in claim 1 wherein the chamber surrounds the contacts.

4. Apparatus as defined in claim 3 wherein the contacts are located near the longitudinal axis of the chamber.

5. Apparatus as defined in claim 1 wherein the first and second flexible layers are formed of material that is substantially inextensible.

6. Apparatus as defined in claim 3 wherein the chamber is remote from the pressure estimation means and wherein the cooperating first and second flexible layers also define fluid passageway means for coupling the chamber surrounding the contacts to the remote pressure estimation means.

7. Apparatus as defined in claim 6 wherein the pressure estimation means includes electrical circuit means for determining remotely whether the contacts are touching or separated.

8. Apparatus as defined in claim 7 wherein the electrical circuit means includes electrically conductive lead means carried by at least one of the cooperating first and second flexible layers.

9. Apparatus as defined in claim 1 wherein the layers defining the chamber have physical dimensions and flexibility selected so that the interposing chamber conforms to the surface of the cuff and does not displace limb surface from the cuff surface.

10. Apparatus for estimating a plurality of pressures applied to a limb by a tourniquet cuff which encircles the limb, comprising:
    a first flexible layer carrying a plurality of first electrical contacts;
    a second flexible layer carrying a plurality of second electrical contacts and cooperating with the first flexible layer to define a flexible pressurizable chamber wherein pairs of first and second electrical contacts are touching when the chamber is not pressurized;
    locating means for attaching the chamber to a tourniquet cuff in a position that interposes the chamber between the cuff and a limb encircled by the cuff and locates the contacts near predetermined cuff locations; and pressure estimation means for selectably increasing the pressure in the chamber and for indicating the lowest selected pressure at which each pair of contacts is separated.

11. Apparatus as defined in claim 10 wherein the pressure estimation means for selectably depressurizing the chamber from a level at which all pairs of contacts are separated, and for indicating each of the highest selected pressures at which corresponding pairs of contacts are touching.

12. Apparatus as defined in claim 10 wherein the chamber surrounds the pairs of contacts.

13. Apparatus as defined in claim 12 wherein the paris of contacts are located near the longitudinal axis of the chamber.

14. Apparatus as defined in claim 13 wherein the chamber is remote from the pressure estimation means and wherein the cooperating first and second flexible layers also define fluid passageway means for coupling the chamber surrounding the contacts to the remote pressure estimation means.

15. Apparatus as defined in claim 14 wherein the pressure estimation means includes electrical circuit means for determining remotely whether the pairs of contacts are touching or separated.

16. Apparatus as defined in claim 15 wherein the electrical circuit means includes electrically conductive lead means carried by at least one of the cooperating first and second flexible layers.

17. Apparatus as defined in claim 10 wherein the layers defining the chamber are comprised of material having a degree of flexibility and physical dimensions selected so that the interposing chamber conforms to the surface of the cuff and does not displace substantially the limb surface from the cuff surface.

* * * * *